(12) United States Patent
Chan

(10) Patent No.: US 6,441,265 B1
(45) Date of Patent: Aug. 27, 2002

(54) WOUND DRESSING

(76) Inventor: Souliya S. Chan, 2033 NW. 19th St., Oklahoma City, OK (US) 73106

( * ) Notice: Subject to any disclaimer, the term of this patent is extended or adjusted under 35 U.S.C. 154(b) by 0 days.

(21) Appl. No.: 09/747,893

(22) Filed: Dec. 26, 2000

(51) Int. Cl.$^7$ .................................................. A61F 13/00
(52) U.S. Cl. .............................. 602/53; 602/41; 602/42; 602/43; 602/56; 602/60
(58) Field of Search .............................. 602/41, 42, 43, 602/44–48, 53, 56, 60, 64, 75; 604/304, 358, 402

(56) References Cited

U.S. PATENT DOCUMENTS

| 3,042,037 A | 7/1962 | Scales et al. | |
|---|---|---|---|
| 3,122,142 A | 2/1964 | Crowe, Jr. | |
| 3,247,845 A | 4/1966 | Kennedy | |
| 3,954,109 A | 5/1976 | Patel | |
| 4,005,709 A | * 2/1977 | Laerdal | 602/53 |
| 4,231,357 A | * 11/1980 | Hessner | 602/47 |
| 4,250,882 A | 2/1981 | Adair | |
| 4,377,159 A | * 3/1983 | Hansen | 602/53 |
| 5,690,610 A | * 11/1997 | Ito et al. | 602/53 |
| 5,800,372 A | * 9/1998 | Bell et al. | 602/48 |
| D403,774 S | 1/1999 | Laughlin et al. | |

* cited by examiner

Primary Examiner—Michael A. Brown
Assistant Examiner—Lalita M. Hamilton

(57) ABSTRACT

A wound dressing for covering a puncture wound caused by drawing of blood. The wound dressing includes a panel that elongated and has a front surface, and a back surface. The panel comprises a flexible material. An adhesive for removably adhering the panel to the skin generally covers the front surface of the panel. An absorbent material for positioning over the cut is securely attached to central a portion of the front surface of the panel. The absorbent material comprises a cotton ball having a generally hemispherical shape such that an outer surface the cotton ball has a convex shape.

1 Claim, 3 Drawing Sheets

WOUND DRESSING

BACKGROUND OF THE INVENTION

1. Field of the Invention

The present invention relates to wound dressings and more particularly pertains to a new wound dressing for covering a puncture wound caused by drawing of blood.

2. Description of the Prior Art

The use of wound dressings is known in the prior art. More specifically, wound dressings heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,042,037; U.S. Pat. No. 3,954,109; U.S. Pat. No. 3,122,142; U.S. Pat. No. 4,250,882; U.S. Pat. No. 3,247,845; Des. U.S. Pat. No. 403,774.

While these devices fulfill their respective, particular objectives and requirements, the aforementioned patents do not disclose a new wound dressing. The inventive device includes a panel that elongated and has a front surface, and a back surface. The panel comprises a flexible material. An adhesive for removably adhering the panel to the skin generally covers the front surface of the panel. An absorbent material for positioning over the cut is securely attached to central a portion of the front surface of the panel. The absorbent material comprises a cotton ball having a generally hemi-spherical shape such that an outer surface the cotton ball has a convex shape.

In these respects, the wound dressing according to the present invention substantially departs from the conventional concepts and designs of the prior art, and in so doing provides an apparatus primarily developed for the purpose of covering a puncture wound caused by drawing of blood.

SUMMARY OF THE INVENTION

In view of the foregoing disadvantages inherent in the known types of wound dressings now present in the prior art, the present invention provides a new wound dressing construction wherein the same can be utilized for covering a puncture wound caused by drawing of blood.

The general purpose of the present invention, which will be described subsequently in greater detail, is to provide a new wound dressing apparatus and method which has many of the advantages of the wound dressings mentioned heretofore and many novel features that result in a new wound dressing which is not anticipated, rendered obvious, suggested, or even implied by any of the prior art wound dressings, either alone or in any combination thereof.

To attain this, the present invention generally comprises a panel that elongated and has a front surface, and a back surface. The panel comprises a flexible material. An adhesive for removably adhering the panel to the skin generally covers the front surface of the panel. An absorbent material for positioning over the cut is securely attached to central a portion of the front surface of the panel. The absorbent material comprises a cotton ball having a generally hemi-spherical shape such that an outer surface the cotton ball has a convex shape.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new wound dressing apparatus and method which has many of the advantages of the wound dressings mentioned heretofore and many novel features that result in a new wound dressing which is not anticipated, rendered obvious, suggested, or even implied by any of the prior art wound dressings, either alone or in any combination thereof.

It is another object of the present invention to provide a new wound dressing which may be easily and efficiently manufactured and marketed.

It is a further object of the present invention to provide a new wound dressing which is of a durable and reliable construction.

An even further object of the present invention is to provide a new wound dressing which is susceptible of a low cost of manufacture with regard to both materials and labor, and which accordingly is then susceptible of low prices of sale to the consuming public, thereby making such wound dressing economically available to the buying public.

Still yet another object of the present invention is to provide a new wound dressing which provides in the apparatuses and methods of the prior art some of the advantages thereof, while simultaneously overcoming some of the disadvantages normally associated therewith.

Still another object of the present invention is to provide a new wound dressing for covering a puncture wound caused by drawing of blood.

Yet another object of the present invention is to provide a new wound dressing which includes a panel that elongated and has a front surface, and a back surface. The panel comprises a flexible material. An adhesive for removably adhering the panel to the skin generally covers the front surface of the panel. An absorbent material for positioning over the cut is securely attached to central a portion of the front surface of the panel. The absorbent material comprises a cotton ball having a generally hemi-spherical shape such that an outer surface the cotton ball has a convex shape.

Still yet another object of the present invention is to provide a new wound dressing that allows a person drawing blood to accomplish the covering of a puncture wound with one device so that tape and cotton balls are not required.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
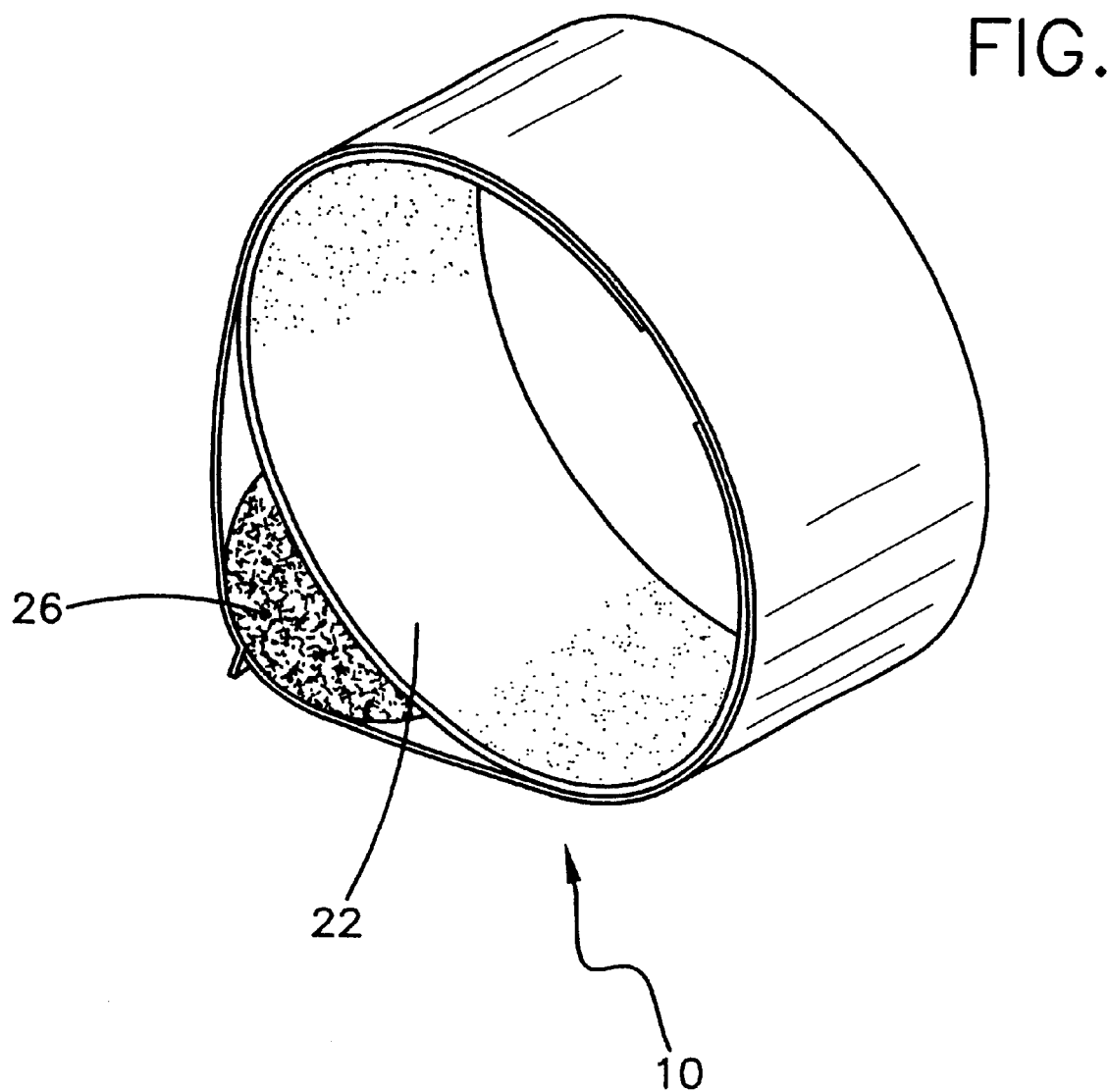
FIG. 1 is a schematic perspective view of a new wound dressing according to the present invention.
Figure 2:
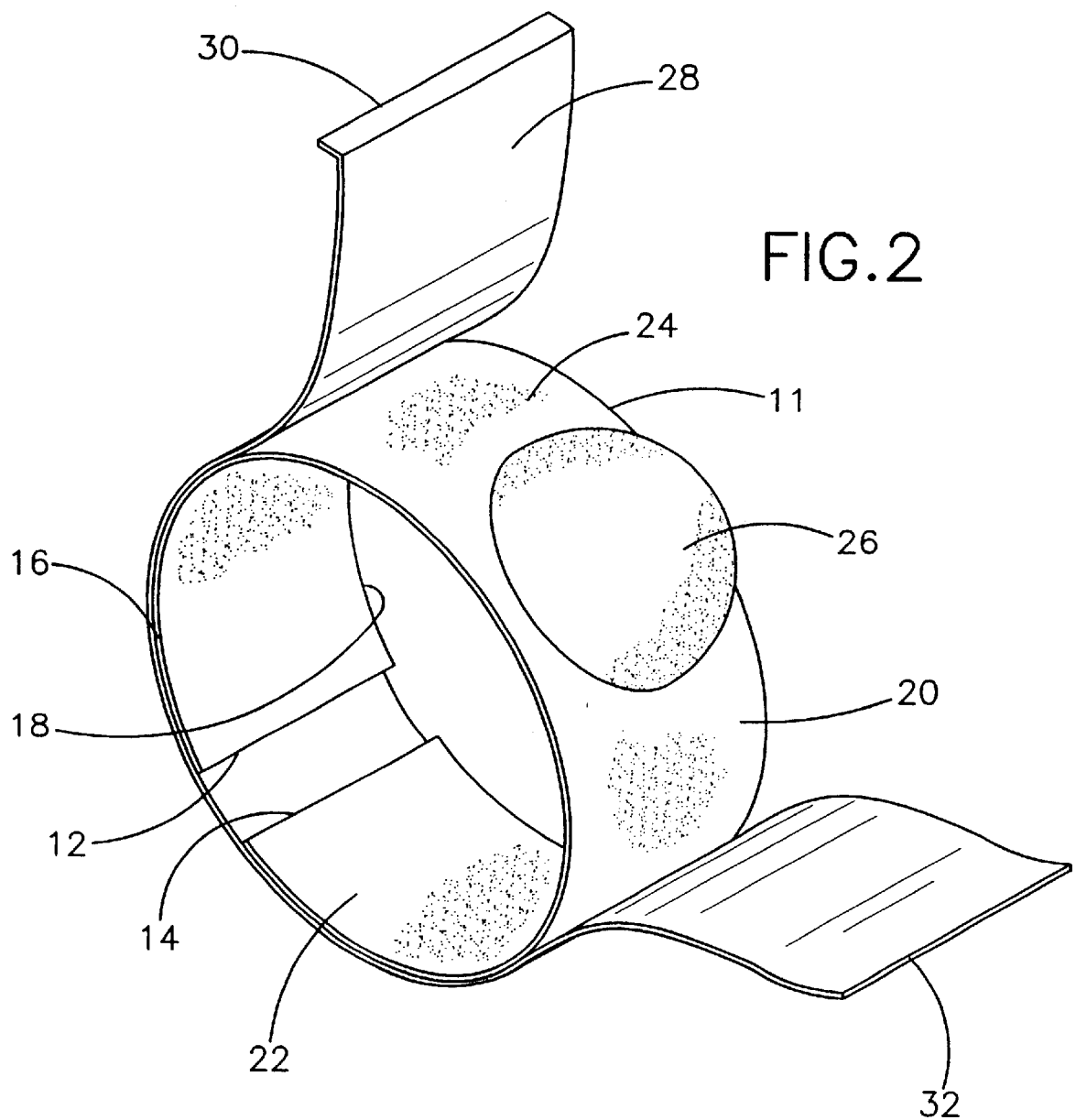
FIG. 2 is a schematic perspective view of the present invention.
Figure 3:
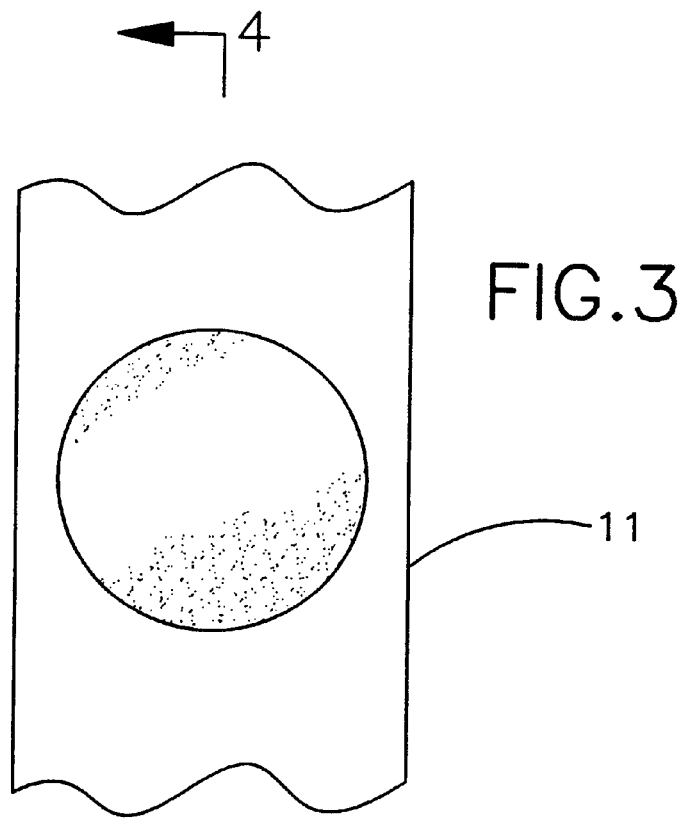
FIG. 3 is a schematic front view of the present invention.
Figure 4:
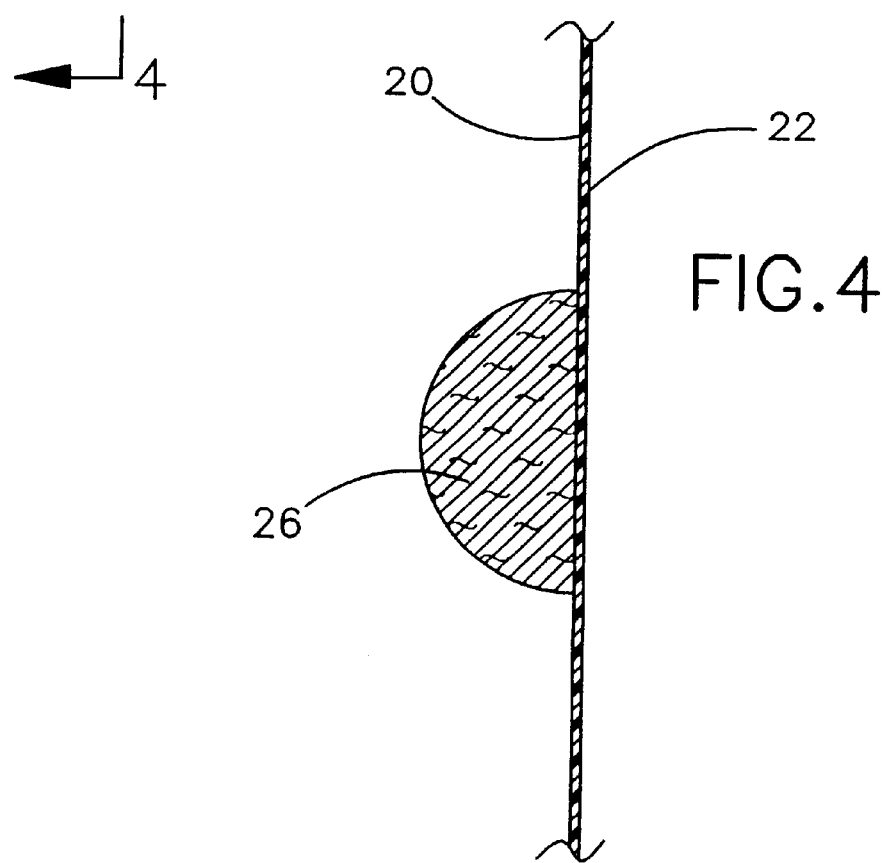
FIG. 4 is a schematic cross-sectional view taken along line 4—4 of the present invention.

With reference now to the drawings, and in particular to FIGS. 1 through 4 thereof, a new wound dressing embodying the principles and concepts of the present invention and generally designated by the reference numeral 10 will be described.

As best illustrated in FIGS. 1 through 4, the wound dressing generally comprises a panel 11 which is elongated and has a first end edge 12, a second end edge 14, a first side edge 16, a second side edge 18, a front surface 20, and a back surface 22. The panel 11 comprises a flexible material. The flexible material is preferably a plastic material. The panel 11 generally has a length generally between 2 inches and 5 inches, and a width generally between ¾ inches and 1½ inches.

An adhesive 24 for removably adhering the panel 11 to the skin generally covers the front surface 20 of the panel 12. The adhesive 24 being a conventional adhesive used on bandages.

An absorbent material 26 for positioning over a cut is securely attached to central a portion of the front surface 20 of the panel 11. The absorbent material 26 comprises a cotton ball having a generally hemi-spherical shape such that an outer surface the cotton ball has a convex shape.

A covering 28 removably covers the adhesive 24. The covering 28 comprises an elongated sheet having a shape substantially identical to the panel 11. The covering 28 has a first end 30 and second end 32. The covering 28 abuts the adhesive 24 such that the first 30 and second 32 ends are positioned adjacent to an apex of the absorbent material 26. The covering 28 substantially covers the absorbent material 26. The panel 11 and the covering 28 are generally curved to define a ring.

In use, the device replaces the conventional cotton ball and tape used to cover a puncture wound caused by drawing blood. The absorbent material is positioned on the wound and the panel adhered to the skin by removing the covering so that the panel abuts the skin.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bandage device, said device being placeable over a cut in skin caused by blood being drawn, said device comprising:

a panel being elongated and having a first end edge, a second end edge, a first side edge, a second side edge, a front surface, and a back surface, said panel comprising a flexible material, said flexible material being a plastic material, said panel having a length generally between 2 inches and 5 inches, said panel having a width generally between ¾ inches and 1½ inches;

an adhesive for removably adhering said panel to the skin, said adhesive generally covering said front surface of said panel;

an absorbent material for positioning over said cut, said absorbent material being securely attached to a central portion of said front surface of said panel, said absorbent material comprising a cotton ball having a generally hemi-spherical shape for inhibiting rolling of said cotton ball between said panel and the skin of the user such that an outer surface of said cotton ball has a convex shape; and a covering for removably covering said adhesive, said covering comprising an elongated sheet having a shape substantially identical to said panel, said covering having a first end and second end, said covering abutting said adhesive such that said first and second ends are positioned adjacent to an apex of said absorbent material, wherein said covering substantially covers said absorbent material, said panel and said covering being generally curved to define a ring.

\* \* \* \* \*